United States Patent [19]

Grober

[11] Patent Number: 6,045,522
[45] Date of Patent: Apr. 4, 2000

[54] CERVICAL SPINE TRACTION APPARATUS

[76] Inventor: Arieh Grober, P.O. Box 21782, 62261 Tel-Aviv, Israel

[21] Appl. No.: 08/963,287

[22] Filed: Nov. 3, 1997

[51] Int. Cl.[7] .......................................................... A61F 5/00
[52] U.S. Cl. .................................................. 602/18; 602/5
[58] Field of Search ................................ 606/61, 60, 241, 606/237; 602/18, 5, 19, 32, 36

[56] References Cited

U.S. PATENT DOCUMENTS 4,987,885  1/1991  Shtabholz .
5,058,572  10/1991  Schmid et al. ............................. 128/75

OTHER PUBLICATIONS

Camp–Wervelkolom–Tractie–Apparaat met Glisson Hoofdbandage Artikel: 2022 (date unknown) 1 pg.
Vertebrace (date unknown) JOBST, 1 pg.
Cervical Collar, Feb. 9, 1997, 1 pg.
New.Improved.Perfit (date unknown), 1 pg.
Back Be Nimble, Plastic Adjustable Cervical Collar (date unknown) 1 pg.
Philadelphia7 Tracheotomy Cervical Collar, Johnson & Johnson Orthopaedics 1 pg. (1996).
FlaManco International, Cervical Collars, Distributor Price List Sep. 25, 1995, 1 pg.
Ortho/Fax, (date unknown) 1 pg.
Zinco Industries, Inc., Pneu–trac Air Pressure the Patient Controls (date unknown) 1 pg.
U.S.M.C.–Minerva–Cervicaalorthese, Artikel: A19–300–00SM (date unknown) 1 pg.

*Primary Examiner*—Richard J. Apley
*Assistant Examiner*—Jayne Saydah
*Attorney, Agent, or Firm*—Arnold B. Silverman; Eckert Seamans Cherin & Mellott, LLC

[57] ABSTRACT

A cervical spine traction apparatus has a generally rearwardly open collar member which has a front portion and a pair of generally rearwardly extending lateral portions. Upwardly open rod supporting housings are provided in the lateral portions. A pair of upwardly extending rods are received within the housing. A rearwardly open chin support is adjustably secured to the rods in overlying relationship with respect to the collar member. The chin support has a front portion and a pair of generally rearwardly extending lateral portions. The chin support may be independently adjusted as to each rod to thereby provide asymmetrical traction to the user or may be so adjusted as to provide symmetrical traction, if desired. A back support member is adjustably secured to the chin support and to the collar member. Such securement may be effected by adjustable straps. The collar member, chin support and back support preferably have rigid body portions with underlying padding. The rods may be mounted for forward and backward movement during adjustment of the apparatus while putting it one the user.

26 Claims, 6 Drawing Sheets

CERVICAL SPINE TRACTION APPARATUS

BACKGROUND OF THE INVENTION

1. Field of the Invention

The present invention provides an apparatus for immobilizing and supporting the cervical spine region and for applying traction thereto and, more specifically, it relates to such apparatus wherein the traction may be applied symmetrical or asymmetrical to the user's cervical spine region.

2. Description of the Prior Art

It has long been known to attempt to alleviate pain in the cervical spine region and adjacent portions of the body resulting from traumatic injuries, degenerative conditions, cervical disc herniation, work related, torticollis, as well as the need to recover from surgical procedures. Numerous types of devices which may be as simple as a flexible or rigid collar which is secured around the neck in chin-supporting relationship have been known. Examples of such cervical collars are those sold under the trade designation Back Be Nimble, Vertebrace and U.S.M.C.-Minerva-Cervicaalorthese. Such devices typically provide only rigid support so as to minimize the extent to which head and neck movement by the user is permitted.

It has also been known to provide adjustability in cervical traction by varying degrees of inflation in a cervical device. Such a product is sold under the trade designation Pneu-trac by Zinco Industries, Inc.

It has also been known to provide traction to the cervical spine area by providing a strap which is fitted under the user's chin and secured to a string or rope which is connected to an overlying support and has at its other end a liquid-containing bag, the weight of which applies traction to the neck. Traction has also been applied to a patient lying in bed by means of weights and ropes or cables.

U.S. Pat. No. 4,987,885, discloses a lumbar traction apparatus which provides independently adjustable traction means between supports secured about the lumbar region of the user. The disclosure of this patent is expressly incorporated herein by reference.

In spite of the foregoing teachings, there remains a need for an efficient apparatus for applying either symmetrical or asymmetrical traction to the cervical spine of a user.

SUMMARY OF THE INVENTION

The present invention provides cervical spine traction apparatus wherein a rearwardly open collar member has a front portion and generally rearwardly extending lateral portions. Upwardly open rod-supporting housings are positioned in the lateral portions with each one supporting an elongated generally rigid rod. A rearwardly open chin support is supported by the rods in overlying relationship with respect to the collar member. The chin support has a front portion and a pair of generally rearwardly extending lateral portions. Each lateral portion of the chin support is secured by adjustment means to a rod which permits independent adjustment of that lateral portion of the chin support with respect to the collar member, thereby permitting the desired traction to be applied independently to each side of the cervical spine traction apparatus.

A back support member for engagement with the cervical spine region is connected to both the chin support and collar member by connection means. The connection means may include first strap means securing an upper portion of the back support to the chin support and second strap means securing a lower portion of the back support to the collar member. The strap means are preferably adjustably securable to the chin support and collar member so as to accommodate different sized necks.

A forwardly facing opening is provided between the collar member and the chin support. A tracheal access opening may be provided within the forward portion of the chin support.

It is an object of the present invention to provide an efficient dynamic cervical spine traction means which is effective in achieving the desired immobilization and facilitates ready control of the traction applied through adjustment by the user or medically trained personnel.

It is another object of the present invention to provide cervical spine traction apparatus which permits asymmetrical traction to be applied when advantageous.

It is a further object of the present invention to provide cervical spine traction apparatus which has the foregoing features and is adjustable to accommodate variations in body size from user to user.

It is another object of the present invention to facilitate the application of traction to the cervical spine region while minimizing or without requiring intervention by medically skilled personnel.

It is a further object of the present invention to provide such apparatus which is made of materials which do not interfere with medical imaging, such as by x-ray or computerized axial tomography.

It is a further object of the invention to provide such apparatus to provide effective arch support while controlling the level of flexion, extension and rotation.

It is a further object of the present invention to provide such a system which has adequate strength and is relatively lightweight.

It is another object of the present invention to provide such a cervical spine traction apparatus which is easy for the user to put on and take off and easy for the user to adjust traction.

It is yet another object of the present invention to provide such a system which has openings to facilitate access therethrough.

These and other objects of the invention will be more fully understood from the following description on reference to the illustrations appended hereto.

DESCRIPTION OF THE PREFERRED EMBODIMENTS

Figure 1:
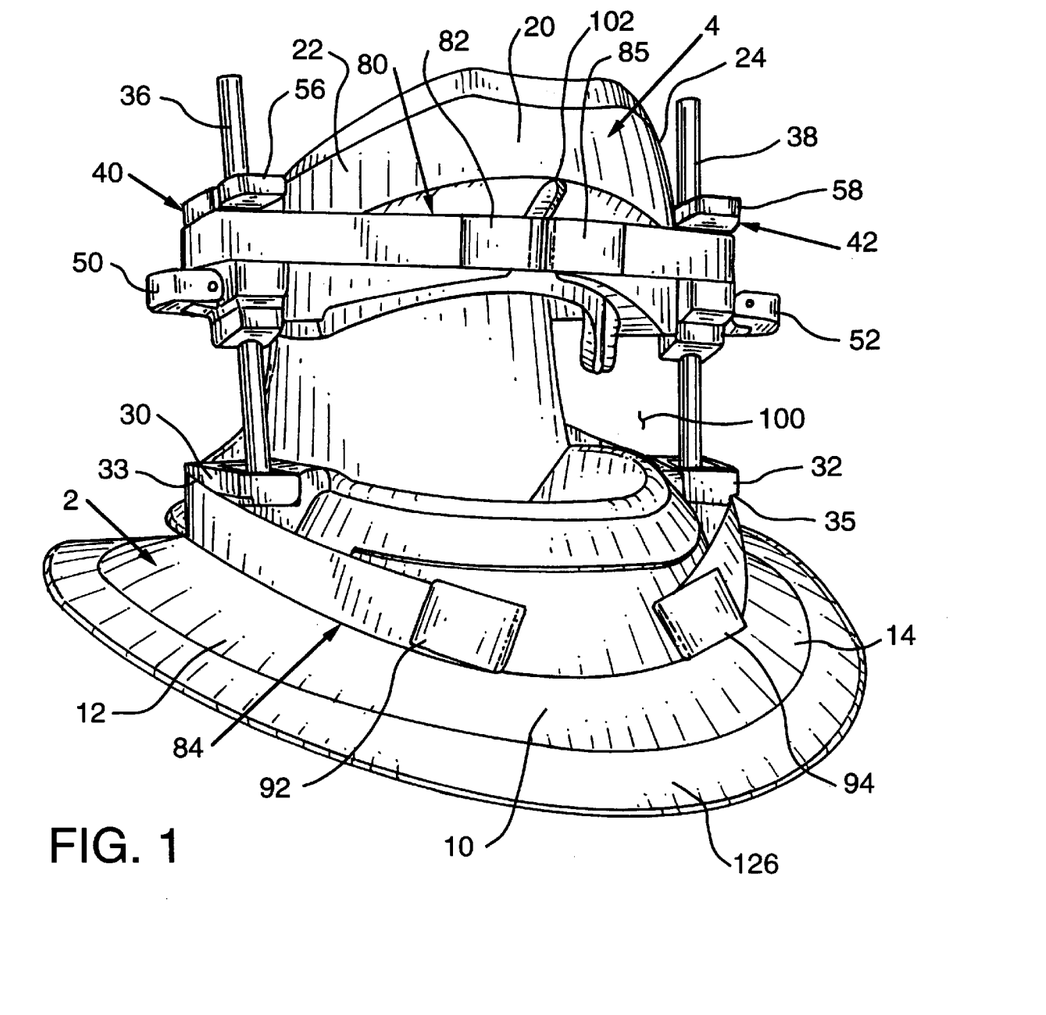
FIG. 1 is a perspective view showing a front portion of the cervical spine traction apparatus of the present invention.
Figure 2:
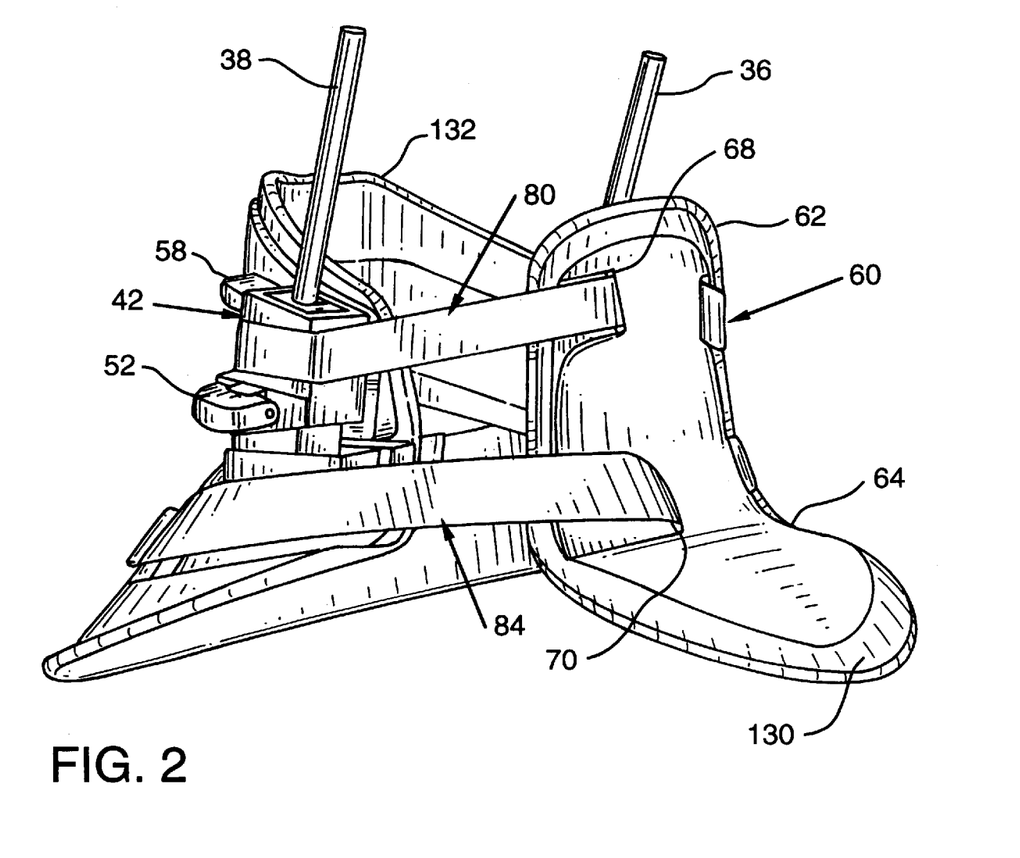
FIG. 2 is a perspective view showing a generally rearward view of the cervical spine apparatus of the present invention.

Referring to FIGS. 1 and 2, there is shown a collar member 2 with an overlying chin support 4 which also supports the jaw of the user. The collar member 2 has a front portion 10 and two lateral portions 12, 14. The chin support 4 has a front portion 20 and two lateral portions 22, 24.

A pair of upwardly open rod-receiving housings 30, 32 are formed respectively within lateral portions 12, 14 of the collar member 2. An elongated substantially rigid rod 36 is secured within housing 30 and an elongated substantially rigid rod 38 is secured within housing 32. These rods may be made of any suitable material, such as steel, stainless steel, aluminum or rigid resinous plastic, for example. The housings 30, 32 may be inserts made of stainless steel or rigid plastic. In the form shown, they also provide for translational movement within housings 30, 32 of the rods 36, 38 traversely as opposed to axial movement of the rods 36, 38 in order to adjust for variations in the position of the straps based upon the size of the user.

Manually operable first adjustment means 40 facilitates locking the chin member 4 to rod 36 at a predetermined location to achieve the desired traction and manually unlocking the same to permit relative movement of the first adjustment means 40 along rod 36. Similarly, second adjustment means 42 facilitates movement along rod 38 to thereby adjust the traction. First adjustment means 40 has a manually operated lever 50 which serves to lock the adjustment means 40 in a desired relative position on rod 36 so as to establish the desired traction on that portion of chin support 4. Similarly, manually operated lever 52 accomplishes the same function on rod 38. As the manually operated levers 50, 52 on the respective adjustments means 40, 42 operate independently, traction may be established either symmetrically or asymmetrically. In order to release the traction, first adjustment means 40 has a release plate 56 and second adjustment means 42 has a release plate 58 which permit full release. The internal structure and functioning of the adjustment means 40, 42 may be conceptually similar in terms of operating components, but different in terms of relative directions of movement of parts from the adjustment means disclosed in U.S. Pat. No. 4,987,885.

Referring still to FIGS. 1 and 2, it will be seen that a back support 60 has an upper portion 62 adapted to engage the cervical spine region and a lower portion 64.

In a preferred embodiment of the invention flexible connecting means are employed to secure the apparatus to the user so as to accommodate for different conditions. neck sizes, head sizes and other variables from user to user. In a preferred embodiment, in order to facilitate case of user putting on and taking off the apparatus, the backrest 60 will have a pair of slots indicated generally by reference number 68 in the upper portion and a pair of slots indicated generally by number 70 in its lower portion. A first strap 80 passes through the slot openings 68 and has its free ends 82, 85 adjustably secured to a forward portion 20 of the chin support 4. This may be accomplished by hook and loop fasteners such as those available under the trade designation VELCRO, for example, or by other means well known to those skilled in the art. Similarly, strap 84 passes through slots 70 in the back support 60 and has its free ends 92, 94 secured adjustably to the forward portion 10 of the collar member 2 as by hook and loop fasteners such as that sold under the trade designation VELCRO, for example. It will be appreciated, therefore, that the relative positions of the collar member 2, chin support 4, and back support 60 may be readily established in the desired position with respect to each other. The straps 80, 84 may advantageously be made of woven nylon fibers or similar, flexible, durable material.

As shown in FIG. 1, an opening 100 is provided in the forward portion of the assembly between the collar member 2 and the chin support 4 to facilitate access to the patient. Also, a tracheotomy opening 102 is provided in the forward portion 20 of the chin support 2.

Figure 3:
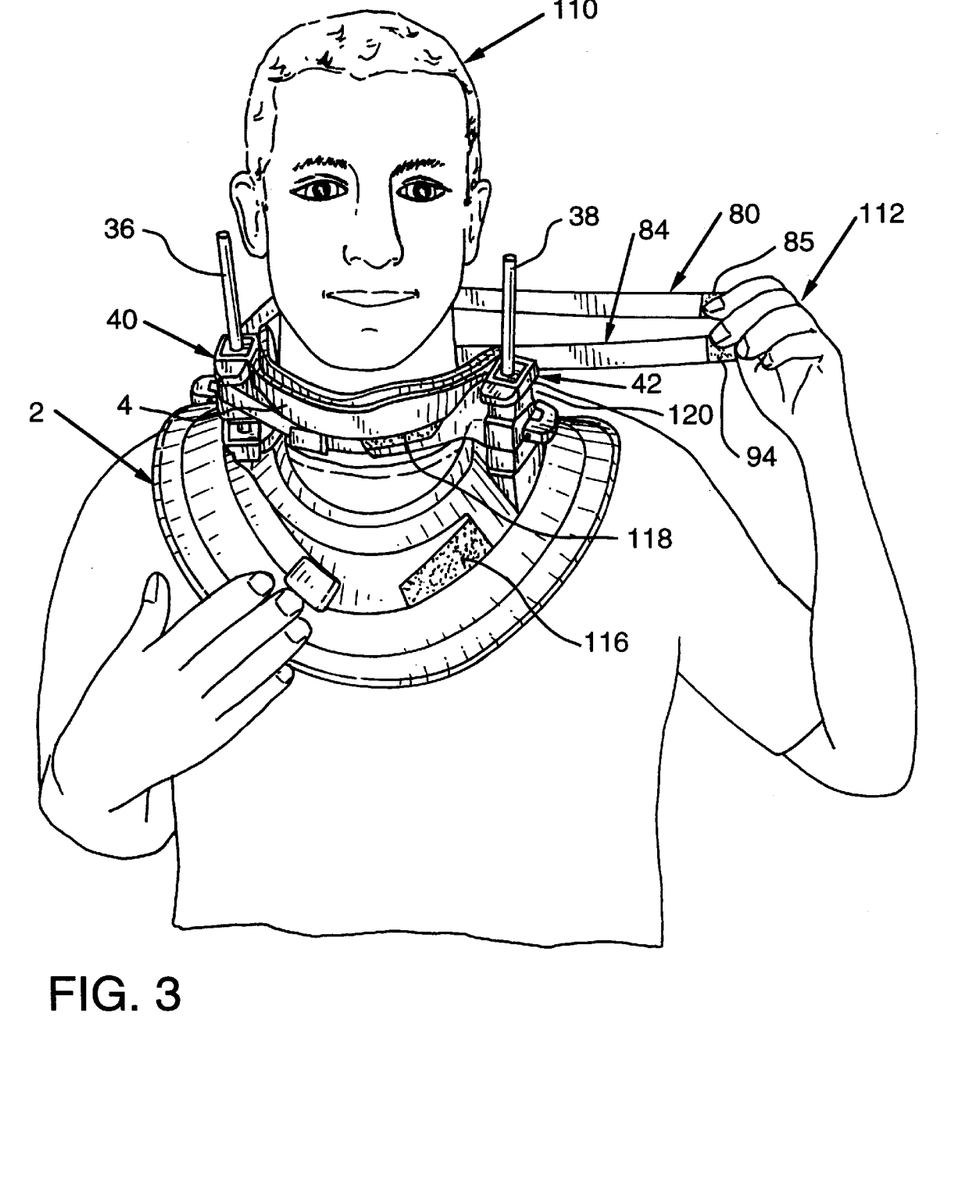
FIG. 3 is a front view showing an individual in the process of putting on the apparatus.

With reference to FIG. 3, a user 110 is shown putting on the apparatus. It will be appreciated that the collar member 2 is structured to be supported by the upper chest portion and shoulders of the user 110. In the form shown in FIG. 3, the chin support 4 is in its lowermost position with respect to collar member 2. The flexible upper strap 80 and the flexible lower strap 84 are held in the user's hand 112. The lower strap 84 will have its end 94 secured to hook or loop portion 116 and the upper strap 80 will have its end 85 secured to hook or loop portion 118. The housings 30, 32 preferably have outwardly open recesses 33, 35, respectively, (FIG. 1) so that the strap ends 84 may be received therein. Similarly, the adjustment means 40, 42 have outwardly open recesses, such as 120 in FIGS. 3 and 6 and 124 in FIG. 7 to receive the strap 84.

Referring to FIGS. 1 through 3, it will be appreciated that the collar member 2, chin support 4, and back support 60 each have a substantially rigid body portion which may be made of vacuum-formed rigid plastic, for example, and have an underlying and adjacent fabric-covered foam padding material 126, 130, 132 which is at least partially interposed between the rigid body portion and the user 110. The padding material is preferably a resiliently compressible resinous foam, such as a polyurethane foam, for example.

As shown in FIGS. 1, 3 and, the strap ends 82, 85, 92, 94 and the manually adjustable means 40, 42, including operating levers 50, 52, 56, 58 are all readily reachable by the user 110 and, therefore, need not require medically skilled personnel to apply or release the apparatus, unless particular circumstances make that desirable.

Figures 5, 6, 7:
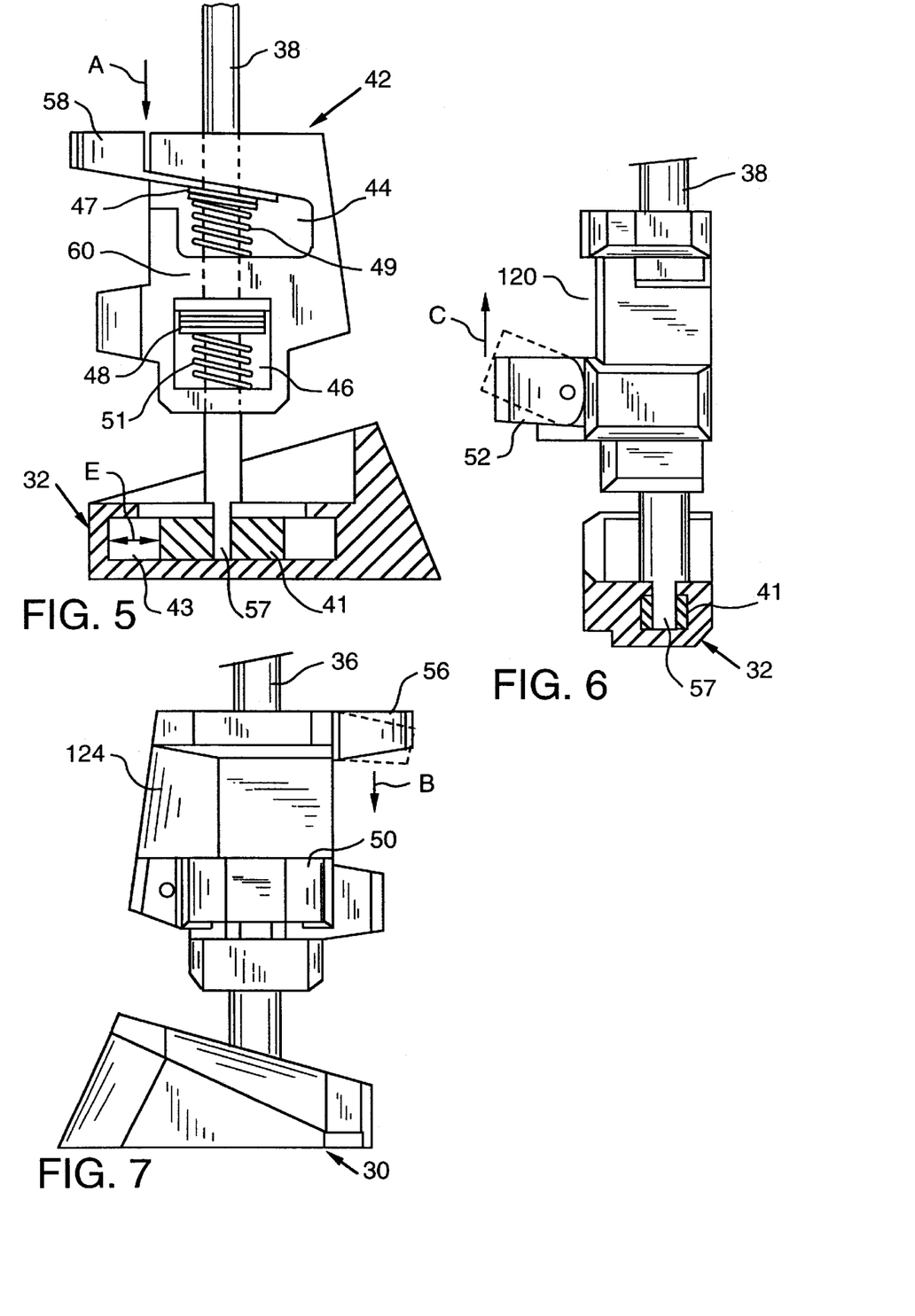
FIG. 5 is an elevational view partly in section of an adjustment means and housing of the present invention.
FIG. 6 is an elevational view partly in section showing a right-side elevational view of the adjustment means, as well as a rod and housing.
FIG. 7 is a right-side elevational view of the adjustment means and housing of the present invention.
Figure 8:
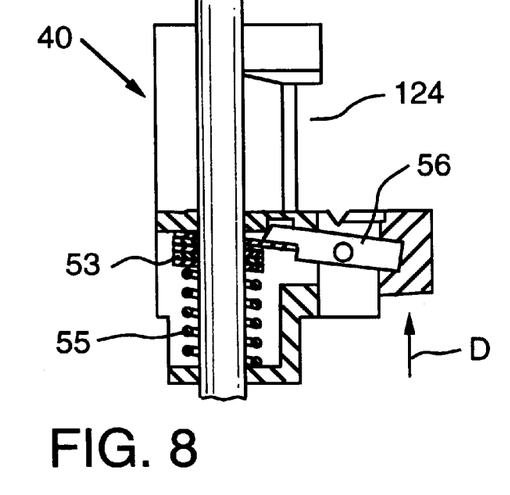
FIG. 8 is an elevational view partly in section of the jack means of the present invention.
Figure 9:
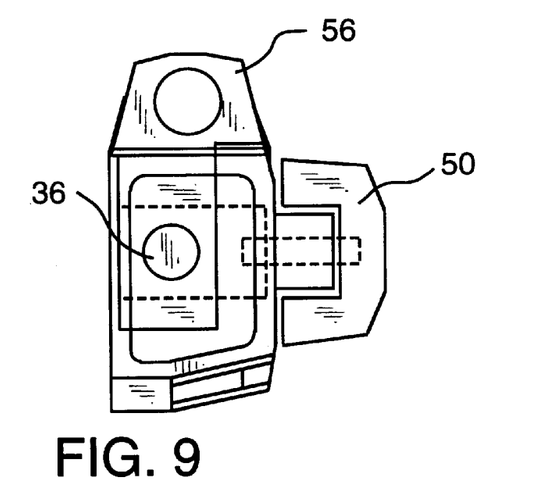
FIG. 9 is bottom plan view of the apparatus of FIG. 8.
Figure 10:
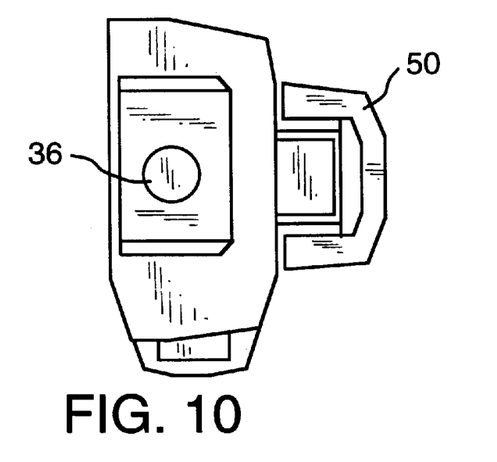
FIG. 10 is a top plan view of the apparatus of FIG. 8.

Referring to FIGS. 5 and 6, a preferred form of housing 32 will be considered. The rod 38 has a lower reduced diameter portion 57 which is intimately received within an opening in runner 41 which, as shown in FIG. 6, is in intimate engagement within a track 43 in the lower portion of housing 32 in terms of movement in a first direction, but has a degree of freedom of movement within the track 43 as shown by arrow E in FIG. 5. This permits the rod 38 to assume a desired position when the apparatus is secured firmly to the user 110.

Referring to FIGS. 5 through 10, the operation of a preferred form of adjustment means 40, 42, will be considered in greater detail. The rod 38 passes through chambers 44, 46 which have a plurality of washers 47, 48, respectively, and underlying coil springs 49, 51 which urge the washers upwardly. In adjustment means 40 (FIG. 8), the washers 53 cooperate with a coil spring 55. By raising operating elements 50, 52 upward, the washers 53, 48 are raised thereby moving the adjustment means 40, 42 upwardly along their respective rods 36, 38 thus lifting the adjustment means 40, 42 and the associated chin support 4. When the release handles 56, 58 are urged downwardly, the washers 47 (FIG. 5) and the corresponding washers (not shown) in adjustment means 42 move downward on the rods 36, 38 (not shown) and the adjustment means 40, 42 move downwardly on the respective rods 36, 38. The handles 50, 52, 56, 58 may advantageously be secured by a suitable mechanical fastener, such as a screw, which permits the desired degree of movement. While it will be appreciated that this is the preferred embodiment in respect of achieving the desired level of traction creation and releasing, other means will be known to those skilled in the art.

The adjustment means, such as 42, have a wall 60 separating chambers 44, 46 with coil spring 49 urging the washers 47 upwardly, as shown in FIG. 5, and coil spring 51 urging the washers 48 upwardly. Moving the release handles 56, 58 (FIGS. 5 and 7) downwardly in the direction shown by arrows A, B, serves to move the washers, such as 47, downwardly on rods 36 or 38 and cause the attaching means 40, 42 to move downwardly on the rods 36, 38. Similarly, movement of the operating levers 50, 52 upwardly in the direction indicated by arrows C and D in FIGS. 6 and 8, respectively, causes the washers 48, 47 to move upwardly under the influence, respectively, of springs 51, 55.

The slot 43 permits movement of runner 41 toward the right or left, as shown in FIG. 5, which corresponds to forward and backward in FIG. 1 to adapt to the tightness of belt 80 corresponding to the adjustment for the individual user's size. The degree of freedom of rod movement in the housings 30, 32 may be about 3 cm in the forward direction from the center position and about 3 cm in the backward position from the center position for a total range of movement of about 6 cm.

As shown in FIGS. 6 and 7, the adjustment means 40, 42 have recesses 124, 120, respectively, for receipt of portions of the strap 80.

While the apparatus may be made from a wide variety of materials, a preferred approach is to have the body of the collar member 2, the chin support 4 and the backrest 60 made of a rigid, resinous, plastic, such as polyurethane or fiber reinforced plastic, for example.

It will be appreciated, therefore, that the present invention provides an effective means for immobilizing and providing traction on either a symmetrical or asymmetrical basis. The user is capable of putting on and removing the apparatus and effecting the desired traction subject to the judgment of medical personnel. The apparatus is designed to have suitable openings for enhanced access to portions of the patient, is of sturdy construction and facilitates ready adjustments in the amount of traction applied to a given patient as well as adjustments as treatment proceeds if desired.

Whereas particular embodiments of the present invention have been described herein for purposes of illustration it will appreciated by those skilled in the art that numerous variations of the details may be made without departing from the invention as described in the appended claims.

I claim:

1. Cervical spine traction apparatus comprising
a rearwardly open collar member having a front portion and a pair of generally rearwardly extending lateral portions,
each collar lateral portion having an upwardly open rod supporting housing,
a generally upwardly extending rod secured within each said housing,
a rearwardly open chin support supported on said rods in overlying relationship with respect to said collar member,
said chin support having a front portion and a pair of generally rearwardly extending chin lateral portions,
said chin support having a first adjustment means which adjustably connects a first said chin lateral portion of said chin support to a first said rod and said first rod remains stationary as the first adjustment means moves relative to said first rod;
said chin support having a second adjustment means which adjustably connects a second said chin lateral portion of said chin support to a second said rod and said second rod remains stationary as the second adjustment means moves relative to said second rod;
a back support for engagement with the user's cervical spine region, and
connection means adjustably securing said back support to said collar member and said chin support;
whereby traction may be applied to the cervical spine through the movement of either said first or second adjustment means relative to said first or second rods, respectively.

2. The cervical spine traction apparatus of claim 1 including
said first adjustment means and said second adjustment means being independently adjustable to permit asymmetrical traction to be applied to the user's cervical spine.

3. The cervical spine traction apparatus of claim 2 including
said connection means including first strap means securing an upper portion of said back support to said chin support and second strap means securing a lower portion of said back support to said collar member.

4. The cervical spine traction apparatus of claim 3 including
said first strap means being an elongated strap passing through said back support and having ends secured to said chin support by hook and loop fastening means.

5. The cervical spine traction apparatus of claim 4 including
said second strap means being an elongated strap passing through said back support and having ends secured to said collar member by hook and loop fastener means.

6. The cervical spine traction apparatus of claim 1 including
said collar member having a substantially rigid body with padding secured to portions thereof.

7. The cervical spine traction apparatus of claim 6 including
said chin support having a substantially rigid body with padding secured to portions thereof.

8. The cervical spine traction apparatus of claim 7 including
said back support having a substantially rigid body with padding secured to portions thereof.

9. The cervical spine traction apparatus of claim 8 including
said padding having portions secured to said collar member, chin support and back support in regions which will contact the user's body.

10. The cervical spine traction apparatus of claim 1 including
said first and second adjustment means each having manually operable means for securing said adjustment means to said rod with the desired level of traction and manually operable release means for releasing the engagement with said rods.

11. Cervical spine traction apparatus comprising
a rearwardly open collar member having a front portion and a pair of generally rearwardly extending lateral portions, each lateral portion having an upwardly open rod supporting housing, a generally upwardly extending rod secured within each said housing, a rearwardly open chin support supported on said rods in overlying relationship with respect to said collar member, said chin support having a front portion and a pair of generally rearwardly extending lateral portions, first adjustment means on said chin support for adjustable connecting a first said lateral portion of said chin support to said rod to permit traction to be applied to the cervical spine through a first lateral portion of said chin support, second adjustment means on said chin support for adjustably connecting a second said lateral portion of said chin support to a second said rod, whereby traction may be applied to the cervical spine, said first adjustment means and said second adjustment means being independently adjustable to permit asymmetrical traction to be applied to the user's cervical spine, a back support for engagement with the user's cervical spine region, connection means adjustably securing said back support to said collar member and said chin support, said connection means including first strap means securing an upper portion of said back support to said chin support and second strap means securing a lower portion of said back support to said collar member, and said first and second adjustment means each having generally outwardly open recesses for receipt of said first strap means.

12. The cervical spine traction apparatus of claim 3 including said lateral portions of said collar member having generally outwardly open recesses for receipt of said second strap means.

13. The cervical spine traction apparatus of claim 1 including said rods being the sole structural connection between said collar member and said chin support.

14. The cervical spine traction apparatus of claim 7 including said body portions of said collar member, said chin support and said back support each being composed of vacuum-formed rigid plastic.

15. The cervical spine traction apparatus of claim 1 including a generally forwardly facing opening disposed between said collar member and said chin support.

16. The cervical spine traction apparatus of claim 1 including said collar member being structured to rest on the user's upper chest and shoulders.

17. The cervical spine traction apparatus of claim 11 including said generally outwardly open recesses in said collar member disposed at least in part on the exterior of said housings.

18. The cervical spine traction apparatus of claim 11 including a tracheal access opening formed within the forward portion of said chin support.

19. Cervical spine traction apparatus comprising a rearwardly open collar member having a front portion and a pair of generally rearwardly extending lateral portions, each lateral portion having an upwardly open rod supporting housing, a generally upwardly extending rod secured within each said housing, a rearwardly open chin support supported on said rods in overlying relationship with respect to said collar member, said chin support having a front portion and a pair of generally rearwardly extending lateral portions, first adjustment means on said chin support for adjustably connecting a first said lateral portion of said chin support to said rod to permit traction to be applied to the cervical spine through a first lateral portion of said chin support, second adjustment means on said chin support for adjustable connecting a second said lateral portion of said chin support to a second said rod, whereby traction may be applied to the cervical spine, a back support for engagement with the user's cervical spine region, connection means adjustably securing said back support to said collar member and said chin support, said first adjustment means and said second adjustment means being independently adjustable to permit asymmetrical traction to be applied to the user's cervical spine, and track means disposed within each said housing to permit horizontal translational movement of the rod received therein.

20. The cervical spine traction apparatus of claim 19 including runner means secured to a lower portion of each said rod disposed within said track means for movement within said track means.

21. Cervical spine traction apparatus comprising a rearwardly open collar member having a front portion and a pair of generally rearwardly extending lateral portions, each lateral portion having an upwardly open rod supporting housing, a generally upwardly extending rod secured within each said housing, a rearwardly open chin support supported on said rods in overlying relationship with respect to said collar member, said chin support having a front portion and a pair of generally rearwardly extending lateral portions, first adjustment means on said chin support for adjustably connecting a first said lateral portion of said chin support to said rod to permit traction to be applied to the cervical spine through a first lateral portion of said chin support, second adjustment means on said chin support for adjustably connecting a second said lateral portion of said chin support to a second said rod, whereby traction may be applied to the cervical spine, said first adjustment means and said second adjustment means being independently adjustable to permit asymmetrical traction to be applied to the user's cervical spine, said first adjustment means and said second adjustment means each having operating levers for raising said adjustment means on said rods and release plates for lowering said adjustment means on said rods.

22. The cervical spine traction apparatus of claim 21 including said first adjustment means and said second adjustment means each having a first chamber operatively associated within said operating lever and a second chamber operatively associated with said release plates.

23. The cervical spine traction apparatus of claim 22 including each said chamber having a plurality of washer elements overlying a compression spring.

24. The cervical spine traction apparatus of claim 23 including said second chambers overlying said first chambers.

25. The cervical spine traction apparatus of claim 23 including said operating lever having a portion extending into said first chamber to effect responsive movement of said first chamber washers against said first chamber compression spring responsive to movement of said operating lever.

26. The cervical spine traction apparatus of claim 23 including said release plate having a portion extending into said first chamber to effect responsive movement of said first chamber washers against said first chamber compression spring responsive to movement of said release plate.

* * * * *

UNITED STATES PATENT AND TRADEMARK OFFICE
CERTIFICATE OF CORRECTION

PATENT NO. : 6,045,522  
DATED : April 4, 2000  
INVENTOR(S) : Arieh Grober

Page 1 of 1

Figure 4:
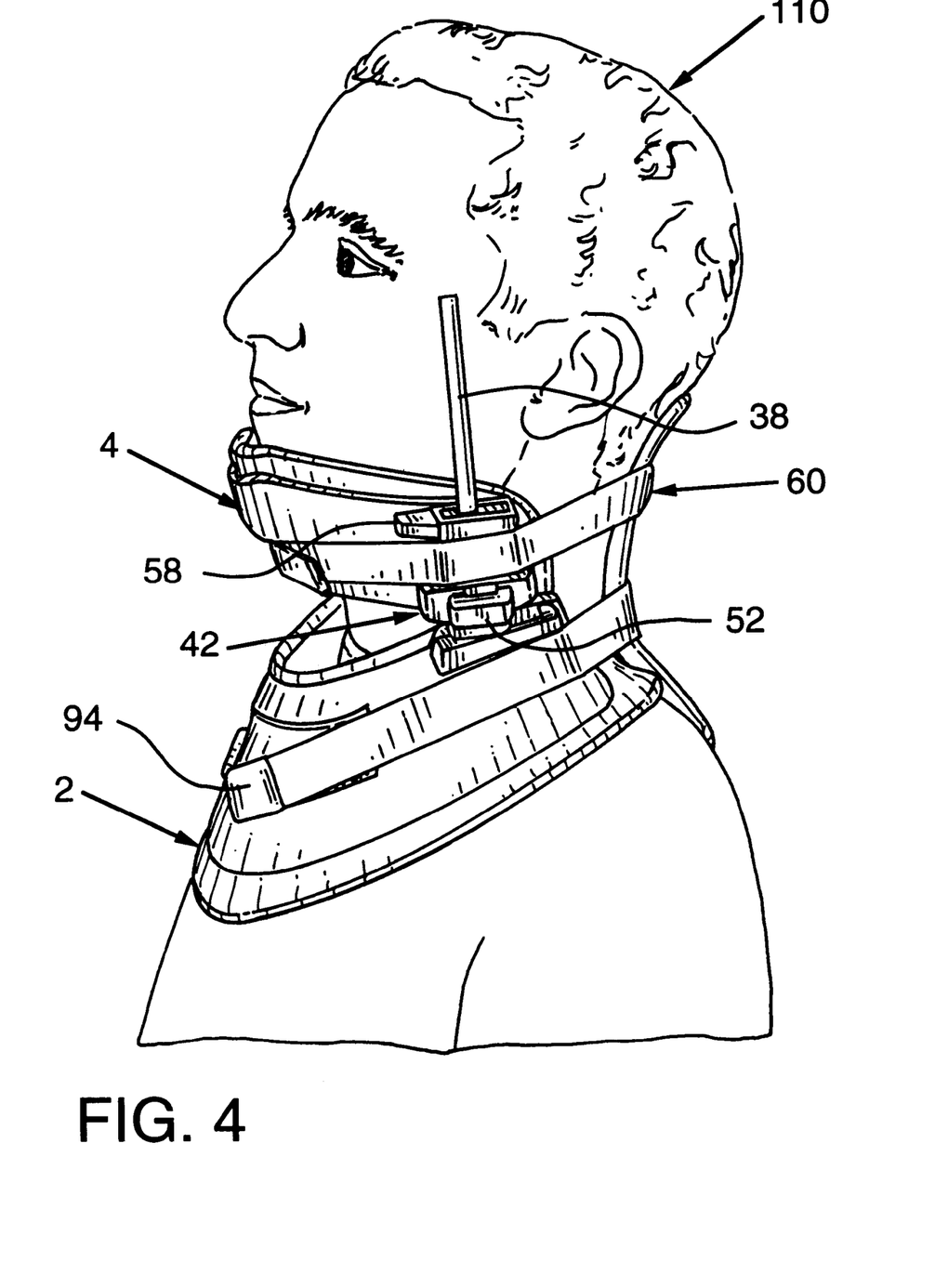
FIG. 4 is a side elevational view showing a user wearing the apparatus.

It is certified that error appears in the above-identified patent and that said Letters Patent is hereby corrected as shown below:

<u>Column 4,</u>  
Line 33, "FIGS. 1,3 and" should read -- FIGS.1, 3 and 4 --.

<u>Column 9,</u>  
Line 9, "within" should read -- with --.

Signed and Sealed this

Twenty-second Day of January, 2002

Attest:

JAMES E. ROGAN  
*Director of the United States Patent and Trademark Office*

*Attesting Officer*